(12) United States Patent
Luff

(10) Patent No.: US 6,239,070 B1
(45) Date of Patent: *May 29, 2001

(54) HERBICIDAL MIXTURES

(75) Inventor: Kelvan Ray Luff, Kimberly, ID (US)

(73) Assignee: Rhone-Poulenc Inc., Research Triangle Park, NC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/095,108

(22) Filed: Jun. 10, 1998

Related U.S. Application Data

(60) Provisional application No. 60/049,280, filed on Jun. 10, 1997.

(51) Int. Cl.⁷ .......................... A01N 25/32; A01N 43/64; A01N 43/00
(52) U.S. Cl. .......................... 504/105; 504/105; 504/134; 504/136
(58) Field of Search .................. 504/105, 134, 504/136

(56) References Cited

U.S. PATENT DOCUMENTS

| | | | | |
|---|---|---|---|---|
| 5,371,064 | * | 12/1994 | Cramp et al. | 504/271 |
| 5,552,367 | * | 9/1996 | Gamblin et al. | 504/138 |
| 5,627,131 | * | 5/1997 | Shribs et al. | 504/107 |
| 5,656,573 | | 8/1997 | Roberts et al. | 504/271 |
| 5,847,146 | * | 12/1998 | Schutze et al. | 546/309 |

FOREIGN PATENT DOCUMENTS

| | | |
|---|---|---|
| 0213892 | 3/1987 | (EP) . |
| 0418175 | 3/1991 | (EP) . |
| 0487357 | 5/1992 | (EP) . |
| 0496630 | 7/1992 | (EP) . |
| 0496631 | 7/1992 | (EP) . |
| 0527036 | 2/1993 | (EP) . |
| 0560482 | 9/1993 | (EP) . |
| 0625505 | 11/1994 | (EP) . |
| 0625508 | 11/1994 | (EP) . |
| 2284547 | * 10/1993 | (GB) . |
| 97/48276 | 12/1997 | (WO) . |

OTHER PUBLICATIONS

Retzinger et al, *Weed Technology*, vol. 11, pp. 384–393 (1997).
The Pesticide Manual ed. C. Tomlin, British Crop Protection Council, England, tenth edition, pp. 32–33, 51–52, 203–205, 239–241, 699–700, 701–702, 734–735, 865–866, 904–905, 913–914, 976–978, 1005–1006, 1010–1011 (1994).
www.weeds.iastate.edu/refernce/siteofaction.htm, Bob Hartzler, Herbicide Site of Action, May 18, 1999, pp. 1–5.
*Chemical Abstracts* 125:161015 (1996).
*Chemical Abstracts* 122:308684 (1994).
*Chemical Abstracts* 119:3010 (1993).
*Chemical Abstracts* 114:116849 (1990).
*Chemical Abstracts* 111:210508 (1989).
*Chemical Abstracts* 111:148749 (1989).
*Chemical Abstracts* 107:170525 (1987).
*Chemical Abstracts* 102:1864 (1984).

\* cited by examiner

*Primary Examiner*—S. Mark Clardy
*Assistant Examiner*—Sabiha N. Qazi
(74) *Attorney, Agent, or Firm*—Burns, Doane, Swecker & Mathis, L.L.P.

(57) ABSTRACT

The invention relates to a method of reducing phytotoxicity in crop plants caused by at least one member of the group consisting of a 4-benzoylisoxazole herbicide and a 2-cyano-1,3-dione herbicide which comprises applying to the locus of the crop plant, the crop or crop plant seed an antidotally effective amount of at least one sulfonylurea herbicide.

59 Claims, No Drawings

HERBICIDAL MIXTURES

CROSS-REFERENCE TO RELATED APPLICATION

This application claims the priority of now abandoned U.S. Provisional Patent Application Ser. No. 60/049,280, filed Jun. 10, 1997, incorporated by reference herein in its entirety and relied upon.

FIELD OF THE INVENTION

This invention relates to a method of safening herbicidal 4-benzoylisoxazoles and 2-cyano-1,3-diones by sulfonylurea herbicides, and to compositions containing the same.

BACKGROUND OF THE INVENTION

It is known that many herbicides injure crop plants at herbicide application rates needed to control weed growth. This renders many herbicides unsuitable for controlling weeds in the presence of certain crops. Where weed growth in crops is uncontrolled however, this results in lower crop yield and reduced crop quality, as weeds will compete with crops for nutrients, light and water. Reduction in herbicidal injury to crops without an unacceptable reduction in the herbicidal action can be accomplished by use of crop protectants known as "safeners", also sometimes referred to as "antidotes" or "antagonists".

4-Benzoylisoxazoles are known to possess herbicidal properties, for example see European Patent Publication Nos. 0418175, 0487357, 0527036 and 0560482. European Patent Publication Nos. 0496630, 0496631, 0625505 and 0625508 disclose certain 1-phenyl-2-cyano-1,3-dione derivatives possessing herbicidal properties. European Patent Publication No. 0213892 discloses herbicidally active enols. These compounds possess very good levels of herbicidal activity, but at higher dose rates there can be a risk of crop phytotoxicity.

The present invention seeks to provide compositions of these herbicides for use in combination with antidotes therefor for reduction of injury to crops, especially wheat, due to phytotoxicity of these herbicides at certain dose rates or under certain conditions of use.

DESCRIPTION OF THE INVENTION

The invention provides a method of reducing phytotoxicity at a crop plant locus caused by at least one 4-benzoylisoxazole herbicide and/or 2-cyano-1,3-dione herbicide which comprises applying to the crop plant locus at least one sulfonylurea herbicide.

Surprisingly, the applicants have found that the presence of at least one sulfonylurea herbicide allows any crop phytotoxicity by the isoxazole and/or 2-cyano-1,3-dione herbicide to be reduced in the presence of at least one sulfonylurea herbicide, while maintaining a good level of weed control.

The method of the invention reduces phytotoxicity by a safening effect of the sulfonylurea. The invention also provides a method whereby the total amount of herbicide may be reduced by virtue of a synergistic effect.

Preferably the 4-benzoylisoxazole herbicide has the general formula (I):

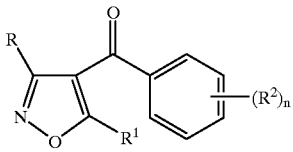

(I)

wherein
R is hydrogen or —$CO_2R^3$;
$R^1$ is $C_{1-6}$ alkyl or $C_{3-6}$ cycloalkyl optionally bearing $C_{1-6}$ alkyl;
$R^2$ is selected from halogen (e.g. chlorine or bromine), —$S(O)_p$Me $CH_2SO_q$Me, $C_{1-6}$ alkyl, $C_{1-6}$ haloalkyl (e.g. $CF_3$), $C_{1-6}$ alkoxy or $C_{1-6}$ haloalkoxy;
n is two or three; p is zero, one or two; q is zero, one or two; and
$R^3$ is $C_{1-4}$ alkyl.

In formula (I) above $R^1$ is preferably cyclopropyl.
In formula (I) above preferably one group $R^2$ represents —$S(O)_p$Me, most preferably in the 2-position of the benzoyl ring.

4-Benzoylisoxazoles of formula (I) above of particular interest in the method of the invention include the following:

A. 5-cyclopropyl-4-(2-methylsulfonyl-4-trifluoromethyl) benzoylisoxazole;

B. ethyl 5-cyclopropyl-4-(2-methylsulfonyl-4-trifluoromethyl)benzoylisoxazole-3-carboxylate;

C. ethyl 5-cyclopropyl-4-[3,4-dichloro-2-(methylthio)-benzoyl]isoxazole-3-carboxylate;

D. 5-cyclopropyl-4-[4-bromo-2-(methylsulfonylmethyl) benzoylisoxazole;

E. 5-cyclopropyl-4-(4-methylsulfonyl-2-trifluoromethyl) benzoylisoxazole; and

F. 5-cyclopropyl-4-(4-chloro-2-methylsulfonyl) benzoylisoxazole.

The letters A to F are assigned to these compounds for reference and identification hereafter.

Compounds A, B and C are preferred.

Preferably the 2-cyano-1,3-dione derivative has the formula (II):

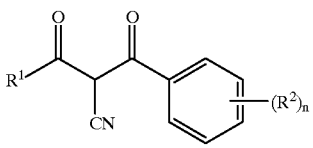

(II)

wherein $R^1$, $R^2$ and n are as defined above.

Compounds of formula (II) above may exist in enolic tautomeric forms that may give rise to geometric isomers around the enolic double bond. Furthermore, in certain cases the groups $R^1$ and $R^2$ may give rise to stereoisomers and geometric isomers. All such forms and mixtures thereof are embraced by the present invention.

The most preferred compound of formula (II) above is 2-cyano-3-cyclopropyl-1-(2-methylsulfonyl-4-trifluoromethylphenyl)propan-1,3-dione.

Preferably the sulfonylurea herbicide has the general formula (III):

$R_4SO_2NR_5C(O)NR_6R_7$ (III)

wherein:

R$_4$ is selected from substituted or unsubstituted phenyl, substituted or unsubstituted thienyl, substituted or unsubstituted pyridyl, and substituted or unsubstituted imidazopyridinyl;

R$_5$ and R$_6$ are independently C$_{1-6}$ alkyl or hydrogen; or

R$_7$ is selected from substituted or unsubstituted triazine or substituted or unsubstituted diazine. Preferably the substituted phenyl, thienyl, pyridyl or imidazopyridinyl moieties are substituted by halogen, alkyl, alkoxy, alkylcarbonyl, alkoxycarbonyl, substituted or unsubstituted amido, alkylthio, alkylsulfenyl, and alkylsulfonyl. The triazine and diazine moieties are preferably substituted by alkoxy or alkyl.

In the above definition, alkyl and moieties comprising it generally contain from one to six carbon atoms and are optionally substituted by one or more atoms from group consisting of bromine, chlorine, fluorine and iodine.

Preferably the sulfonylurea herbicide has the general formula (III) with one or more of the following features:

R$_4$ is selected from 2-substituted phenyl, 2-substituted-3-thienyl, 3-substituted-2-pyridyl; 2-substituted-imidazo[1,2-a]pyridine;

R$_5$ and R$_6$ are independently methyl or hydrogen; and

R$_7$ is selected from 4,6-dimethoxy-1,3,5-triazine; 4-methoxy-6-methyl-1,3,5-triazine; 4,6-bisdifluoromethoxy-1,3-diazine, and 4,6-dimethoxy-1,3-diazine.

Even more preferably the sulfonylurea herbicide has the general formula (III) wherein:

R$_4$ is selected from 2-chlorophenyl; 2-methoxycarbonylphenyl, 2-haloalkylphenyl, 2-haloalkoxyphenyl, 2-methoxycarbonyl-3-thienyl, 3-dialkylamido-2-pyridyl and 2-alkylsulfonylimidazo[1,2-a]pyridine;

R$_5$ and R$_6$ are independently selected from hydrogen or methyl; and

R$_7$ is selected from 4,6-dimethoxy-1,3,5-triazine; 4-methoxy-6-methyl-1,3,5-triazine; 4,6-bisdifluoromethoxy-1,3-diazine; and 4,6-dimethoxy-1,3-diazine.

Preferably there are one or two sulfonylurea herbicides present selected from:

1-(2-chlorophenylsulfonyl)-3-(4-methoxy-6-methyl-1,3,5-triazin-2-yl)urea(chlorsulfuron);

2-[4-methoxy-6-methyl-1,3,5-triazin-2-yl(methyl)carbamoylsulfamoyl]benzoic acid (tribenuron-methyl);

3-(4-methoxy-6-methyl-1,3,5-triazin-2-ylcarbamoylsulfamoyl)thiophen-2-carboxylic acid (thifensulfuron methyl);

2-(4-methoxy-6-methyl-1,3,5-triazin-2-ylcarbamoylsulfamoyl)benzoic acid (metsulfuron);

1-[2-(2-chloroethoxy)phenylsulfonyl]-3-(4-methoxy-6-methyl-1,3,5-triazin-2-yl)urea (triasulfuron);

1-(4-methoxy-6-methyl-1,3,5-triazin-2-yl)-3-[2-(3,3,3-trifluoropropyl)-phenylsulfonyl]urea (CGA-152005 or prosulfuron);

1-(4,6-dimethoxypyrimidin-2-yl)-3-(3-dimethylcarbamoyl-2-pyridylsulfonyl)urea (nicosulfuron);

2-[4,6-bis(difluoromethoxy)pyrimidin-2-yl-carbamoylsulfamoyl]benzoic acid (primisulfuron);

N-[[(4,6-dimethoxy-2-pyrimidinyl)amino]carbonyl]-3-ethylsulfonyl-2-pyridinesulfonamide (rimsulfuron or DPX-E9636) and 1-(2-ethylsulfonylimidazo[1,2-a]pyridin-3-ylsulfonyl)-3-(4,6-dimethoxypyrimidin-2-yl)urea (MON 37500: CAS Registry Number 141776-32-1).

Sulfonylurea herbicides may be prepared by references found in The Pesticide Manual, 10$^{th}$ Edition, C. Tomlin editor; British Crop Protection Association, 1994, or by those known to the skilled addressee.

Most preferably there are two sulfonyl urea herbicides present. Preferably these are selected from thifensulfuron methyl, tribenuron methyl and MON 37500.

The amount of sulfonylurea herbicide used in the method of the invention varies according to a number of parameters including the weeds to be controlled, the crop to be protected, the amount and rate of herbicide applied, and the edaphic and climatic conditions prevailing. Also, the selection of the specific antidotes for use in the method of the invention, the manner in which it is to be applied and the determination of the activity which is non-phytotoxic but antidotally effective, can be readily performed in accordance with common practice in the art.

By "non-phytotoxic" is meant an amount of the antidote which causes at most minor or no injury to the desired crop species. By "antidotally effective" is meant an antidote used in an amount which is effective as an antidote to decrease the extent of injury caused by the herbicide to the desired crop species.

The dose rate of the benzoylisoxazole herbicide and/or 2-cyano-1,3-dione herbicide is generally from about 5 to about 500 grams per hectare (g/ha), preferably from about 15 to about 200 g/ha, more preferably from about 20 to about 120 g/ha, even more preferably from about 70 to about 90 g/ha.

The dose rate of the sulfonylurea herbicide is generally from about 1 to about 250 g/ha, preferably from about 1 to about 100 g/ha, more preferably from about 3 to about 20 g/ha and even more preferably from about 5 to about 15 g/ha.

Preferably the weight ratio of isoxazole/dione:sulfonylurea herbicide is from about 500:1 to about 1:50, preferably from about 200:1 to about 1:7, more preferably from about 40:1 to about 1:1, and even more preferably from about 18:1 to about 5:1.

The method of the invention can be applied pre- or post-emergence of the crop. Where the crop is a cereal crop (such as wheat) the herbicide is preferably applied post-emergence of the crop species.

In one advantageous aspect, the present invention provides a method for reducing phytotoxicity in a crop plant in need of same, said phytotoxicity in said crop plant resulting from treatment with a 4-benzoylisoxazole herbicide or a 2-cyano-1,3-dione herbicide, said method comprising applying to said crop plant, to its locus or to its seed:

(a) a herbicidally effective amount, sufficient to elicit phytotoxicity in said crop plant, of at least one member selected from the group consisting of a 4-benzoylisoxazole herbicide and a 2-cyano-1,3-dione herbicide; and (b) an effective phytotoxicity-reducing amount of at least one sulfonylurea herbicide.

Preferably, both (a) and (b) are applied to the crop plant or to its locus, but the invention also contemplates application of (a) and (b) to the seed. It is also preferred that (a) and (b) are applied together, or separately but in close time proximity to each other. However, the invention also contemplates that a greater time lapse between application of (a) on the one hand and (b) on the other is possible. In some instances, it is believed to be possible to apply one of (a) and (b) to the seed and the other to the plant or locus, depending upon the particular crop, and still achieve the desired reduction of phytotoxicity.

According to a further feature of the present invention there is provided a composition comprising:
- (a) at least one 4-benzoylisoxazole herbicide or 2-cyano-1,3-dione herbicide; and
- (b) at least one sulfonylurea herbicide,
  in association with an agriculturally acceptable diluent or carrier and/or optionally a surface active agent. Typically, a herbicidally effective amount of the benzoylisoxazole/cyanodione and an effective phytotoxicity-reducing amount of the sulfonylurea are present. In one embodiment, the phytotoxicity-reducing amount of the sulfonylurea is an amount which is less than that at which the sulfonylurea is herbicidally effective. Also, the herbicidally effective amount of the benzoylisoxazole/cyanodione is generally an amount sufficient to elicit phytotoxicity in the target crop plant. The composition may be provided as a ready-to-use formulation (e.g. where (a) and (b) are premixed), or may be formed as a tank mix in accordance with standard techniques in the art.

The herbicidal action of the composition may be substantially higher than the sum of the effects of the individual agents. The effect may be a synergistic effect. The synergistic combinations and compositions of the invention comprise a synergistic herbicidally effective amount of:
- (a) at least one member selected from the group consisting of a 4-benzoylisoxazole herbicide and a 2-cyano-1,3-dione herbicide; and
- (b) at least one sulfonylurea herbicide.

The synergistic compositions further comprise an agriculturally acceptable diluent or carrier and/or a surface-active agent. In the synergistic combinations and compositions, the weight ratio of (a): (b) is preferably from about 500:1 to about 1:50, more preferably from about 200:1 to about 1:7, even more preferably from about 100:1 to about 1:1, still more preferably from about 40:1 to about 1:1, and most preferably from about 18:1 to about 5:1.

The composition according to the invention can be used both in conventional methods of cultivation (strip cultivation with suitable strip width) and in plantation cultivation (e.g., vines, fruit, citrus), as well as in industrial plants and track systems, on roads and squares, but also to handle stubble and in the minimum-tillage method. They are also suitable as burners (for killing foliage, e.g. in potatoes) or as defoliants (e.g. in cotton). They are also suitable for use on fallow areas. Other areas of use are in tree nurseries, forests, grasslands, and in the cultivation of ornamental plants.

Examples of weeds which can be combatted well by the agents or combinations of agents according to the invention are:

Dicotyledon weeds of the genera sinapis, lepidium, galium, stellaria, matricaria, anthemis, galinsoga, chenopodium, urtica, senecio, amaranthus, portulaca, xanthium, convolvulus, ipomoca, polygonum, sesbania, ambrosia, solanum, cirsium, carduus, sonchus, rorippa, rotaia, lindernia, lamium, veronica, abutilon, emex. sida, datura, viola, galeopsis, papaver, centaurea, trifolium, ranunculus, taraxum, and mentha.

Monocotyledon weeds of the genera echinochloa, setaria, panicum, digitaria, phleum, poa, festuca, eleusine, brachiaria, lolium, bromus, avena, cyperus, sorghum, agropyron, cynodon, monochoria, fimbristylis, sagittaria, eleocharis, scirpus, papalum, ischaemum, spenoclea, dactyloctenium, agrostis, alopecurus, apera.

However, the use of the agents and combinations of agents according to the invention is in no way limited to these genera, but rather extends in the same way to other plants.

The crops that may be protected by the method of the invention include corn, rice, wheat, soya, sorghum and cotton. The method of the invention is preferably performed where the crop to be protected is wheat.

The invention also provides a product comprising at least one 4-benzoylisoxazole herbicide and/or 2-cyano-1,3-dione herbicide and a sulfonylurea herbicide for simultaneous, separate or sequential use in the control of weeds at a locus.

The following non-limiting Examples illustrate the invention.

EXAMPLE 1

Compositions containing Compound A (formulated as a wettable powder containing 75% active ingredient) alone, in tank-mixture with Triton Ag 98 (trademark, 0.25% v/v; a non-ionic surfactant) and in tank-mixture with Triton Ag 98, thifensulfuron methyl and tribenuron methyl were mixed together in a spray tank (the latter two sulfonylurea herbicides were used as the commercial formulation HARMONY EXTRA™ a wettable powder containing 75% combined active ingredients) were sprayed at a volume of 225 liters per hectare over Penawawa Soft White Spring Wheat which had emerged from seeding and grown to a height of about 18 cm. Comparative ratings for damage (by visual inspection of the degree of chlorosis present) to the wheat were taken at 4 and 8 days after treatment (DAT) in comparison with untreated control. The following results were observed:

|  |  | Percent Chlorosis | |
| --- | --- | --- | --- |
| Mixture | Rate Active Ingredient (g/ha) | 4 DAT | 8 DAT |
| Compound A | 70 | 0 | 0 |
| Compound A + Triton AG 98 | 70 | 23 | 60 |
| Compound A + Triton AG 98 Thifensulfuron methyl Tribenuron methyl | 70 11.6 5.8 | 15 | 37 |

EXAMPLE 2

The same procedure as described in Example 1 was followed replacing Compound A with Compound B (which was formulated as a suspension concentrate containing 4% active ingredient). The following results were obtained.

|  |  | Percent Chlorosis | |
| --- | --- | --- | --- |
| Mixture | Rate Active Ingredient (g/ha) | 4 DAT | 8 DAT |
| Compound B | 85 | 0 | 0 |
| Compound B + Triton Ag 98 | 85 | 18 | 38 |
| Compound B + Triton Ag 98 Thifensulfuron methyl Tribenuron methyl | 85 11.6 5.8 | 11 | 20 |

EXAMPLE 3

Compound C as a 25% emulsifiable concentrate and prosulfuron (as a 20% wettable powder) were suspended in tap water and applied post-emergence both alone and in combination at a range of concentrations to *Xanthium strumarium*, *Amaranthus retroflexus*, and *Setaria faberi*. Treatment effects were assessed visually 20 days after treatment. The percentage damage compared to untreated controls was recorded for each species.

The nature of the interaction between the two components was determined using the responses of the herbicides applied singly in calculating the expected response when they are combined (COLBY, S. R., "Calculating synergistic and antagonistic response of herbicide combinations". Weeds 15, pages 20–22, 1967):

$$We = X + \frac{Y \cdot (100 - X)}{100}$$

wherein

X=Percentage mortality, compared with untreated controls, after treatment with Compound C at a rate of application of p g/hectare.

Y=Percentage mortality, compared with untreated controls, after treatment with prosulfuron at a rate of application of q g/hectare.

We=The expected pesticidal activity (percentage mortality compared with untreated controls) after treatment with Compound C and prosulfuron at a rate of application of p+q g/ha.

In the tables that follow the figures used for weed control are percentages reduction in growth when compared with untreated controls. The figures in parentheses are those expected using the Colby formula.

TABLE 1

Post-emergence treatment of *Xanthium strumarium* with various mixtures of Compound C and prosulfuron

| | | Prosulfuron | | | | |
|---|---|---|---|---|---|---|
| | Dose g/ha | 0 | 1 | 2 | 4 | 8 |
| Cpd C | 0 | — | 0 | 15 | 0 | 55 |
| | 8 | 0 | 5(0) | 15(15) | 25(0) | 65(55) |
| | 16 | 5 | 25(5) | 40(19) | 60(5) | 90(57) |
| | 32 | 15 | 20(15) | 45(28) | 45(15) | 87(62) |
| | 63 | 20 | 30(20) | 35(32) | 62(20) | 77(64) |
| | 125 | 40 | 55(40) | 85(49) | 80(40) | 95(73) |

TABLE 2

Post-emergence treatment of *Amaranthus retroflexus* with various mixtures of Compound C and prosulfuron

| | | Prosulfuron | | |
|---|---|---|---|---|
| | Dose g/ha | 0 | 4 | 8 |
| Cpd C | 0 | — | 20 | 35 |
| | 8 | 20 | 60(36) | 77(48) |
| | 16 | 40 | 60(52) | 75(61) |
| | 32 | 52 | 82(62) | 87(69) |

TABLE 3

Post-emergence treatment of *Setaria faberi* with various mixtures of Compound C and prosulfuron

| | | Prosulfuron | | | | |
|---|---|---|---|---|---|---|
| | Dose g/ha | 0 | 1 | 2 | 4 | 8 | 16 |
| Cpd C | 0 | — | 0 | 5 | 20 | 20 | 32 |
| | 16 | 35 | 50(35) | 50(38) | 60(48) | 60(48) | 75(56) |

For a range of mixtures of Compound C with prosulfuron against *Xanthium strumarium, Amaranthus retroflexus* and *Setaria faberi* the observed response was greater than expected response thus indicating synergism.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for reducing phytotoxicity in a crop plant in need of same, said phytotoxicity in said crop plant resulting from treatment with a 4-benzoylisoxazole herbicide, said method comprising applying to said crop plant, to its locus or to its seed:

(a) a herbicidally effective amount, sufficient to elicit phytotoxicity in said crop plant, of a 4-benzoylisoxazole herbicide selected from the group consisting of:

5-cyclopropyl-4-(2-methylsulfonyl-4-trifluoromethyl) benzoylisoxazole; ethyl 5-cyclopropyl-4-(2-methylsulfonyl-4-trifluoromethyl)benzoylisoxazole-3-carboxylate;

ethyl 5-cyclopropyl-4-[3,4-dichloro-2-(methylthio) benzoylisoxazole-3-carboxylate;

5-cyclopropyl-4-[4-bromo-2-(methylsulfonylmethyl) benzoylisoxazole;

5-cyclopropyl-4-(4-methylsulfonyl-2-trifluoromethyl) benzoylisoxazole; and 5-cyclopropyl-4-(4-chloro-2-methylsulfonyl) benzoylisoxazole; and (b) an effective phytotoxicity-reducing amount of at least one sulfonylurea herbicide selected from the group consisting of:

1-(2-chlorophenylsulfonyl)-3-(4-methoxy-6-methyl-1,3,5-triazin-2-yl)urea;

2-[4-methoxy-6-methyl-1,3,5-triazin-2-yl(methyl) carbamoylsulfamoyl]benzoic acid;

3-(4-methoxy-6-methyl-1,3,5-triazin-2-ylcarbamoylsulfamoyl)thiophen-2-carboxylic acid;

2-(4-methoxy-6-methyl-1,3,5-triazin-2-ylcarbamoylsulfamoyl)benzoic acid;

1-[2-(2-chloroethoxy)phenylsulfonyl]-3-(4-methoxy-6-methyl-1,3,5-triazin-2-yl)urea;

1-(4-methoxy-6-methyl-1,3,5-triazin-2-yl)-3-[2-(3,3,3-trifluoropropyl)-phenylsulfonyl]urea;

1-(4,6-dimethoxypyrimidin-2-yl)-3-(3-dimethylcarbamoyl-2-pyridylsulfonyl)urea;

2-[4,6-bis(difluoromethoxy)pyrimidin-2-yl-carbamoylsulfamoyl]benzoic acid;

N-[[(4,6-dimethoxy-2-pyrimidinyl)amino]carbonyl]-3-ethylsulfonyl-2-pyridinesulfonamide; and 1-(2-ethylsulfonylimidazo[1,2-a]pyridin-3-ylsulfonyl)-3-(4,6-dimethoxypyrimidin-2-yl)urea;

the weight ratio of (a) to (b) being from about 500:1 to about 1:50.

2. A method according to claim 1, wherein the sulfonylurea herbicide (b) reduces phytotoxicity by eliciting a safening effect.

3. A method according to claim 1, wherein the sulfonylurea herbicide (b) reduces phytotoxicity by eliciting a synergistic herbicidal effect with herbicide (a) sufficient to enable lowering of the total amount of herbicide applied.

4. A method according to claim 2, wherein the sulfonylurea herbicide (b) reduces phytotoxicity by eliciting a synergistic herbicidal effect with herbicide (a) sufficient to enable lowering of the total amount of herbicide applied.

5. A method for reducing phytotoxicity in a crop plant in need of same, said phytotoxicity in said crop plant resulting from treatment with a 4-benzoylisoxazole herbicide, said method comprising applying to said crop plant or to its locus:

(a) a herbicidally effective amount, sufficient to elicit phytotoxicity in said crop plant, of a 4-benzoylisoxazole herbicide selected from the group consisting of:
5-cyclopropyl-4-(2-methylsulfonyl-4-trifluoromethyl) benzoylisoxazole;
ethyl 5-cyclopropyl-4-(2-methylsulfonyl-4-trifluoromethyl)benzoylisoxazole-3-carboxylate; and
ethyl 5-cyclopropyl-4-[3,4-dichloro-2-(methylthio) benzoylisoxazole-3-carboxylate; and (b) an effective phytotoxicity-reducing amount of at least one sulfonylurea herbicide selected from the group consisting of:
1-(2-chlorophenylsulfonyl)-3-(4-methoxy-6-methyl-1, 3,5-triazin-2-yl)urea;
2-[4-methoxy-6-methyl-1,3,5-triazin-2-yl(methyl) carbamoylsulfamoyl]benzoic acid;
3-(4-methoxy-6-methyl-1,3,5-triazin-2-ylcarbamoylsulfamoyl)thiophen-2-carboxylic acid;
2-(4-methoxy-6-methyl-1,3,5-triazin-2-ylcarbamoylsulfamoyl)benzoic acid;
1-[2-(2-chloroethoxy)phenylsulfonyl]-3-(4-methoxy-6-methyl-1,3,5-triazin-2-yl)urea;
1-(4-methoxy-6-methyl-1,3,5-triazin-2-yl)-3-[2-(3,3,3-trifluoropropyl)-phenylsulfonyl]urea;
1-(4,6-dimethoxypyrimidin-2-yl)-3-(3-dimethylcarbamoyl-2-pyridylsulfonyl)urea;
2-[4,6-bis(difluoromethoxy)pyrimidin-2-yl-carbamoylsulfamoyl]benzoic acid;
N-[[(4,6-dimethoxy-2-pyrimidinyl)amino]carbonyl]-3-ethylsulfonyl-2-pyridinesulfonamide; and
1-(2-ethylsulfonylimidazo[1,2-a]pyridin-3-ylsulfonyl)-3-(4,6-dimethoxypyrimidin-2-yl)urea;
the weight ratio of (a) to (b) being from about 500:1 to about 1:50.

6. A composition comprising:
(a) a herbicidally effective amount, sufficient to elicit phytotoxicity in a crop plant, of a 4-benzoylisoxazole herbicide selected from the group consisting of:
5-cyclopropyl-4-(2-methylsulfonyl-4-trifluoromethyl) benzoylisoxazole;
ethyl 5-cyclopropyl-4-(2-methylsulfonyl-4-trifluoromethyl)benzoylisoxazole-3-carboxylate;
ethyl 5-cyclopropyl-4-[3,4-dichloro-2-(methylthio) benzoylisoxazole-3-carboxylate;
5-cyclopropyl-4-[4-bromo-2-(methylsulfonylmethyl) benzoylisoxazole;
5-cyclopropyl-4-(4-methylsulfonyl-2-trifluoromethyl) benzoylisoxazole; and
5-cyclopropyl-4-(4-chloro-2-methylsulfonyl) benzoylisoxazole; and (b) an effective phytotoxicity-reducing amount of at least one sulfonylurea herbicide selected from the group consisting of:
1-(2-chlorophenylsulfonyl)-3-(4-methoxy-6-methyl-1, 3,5-triazin-2-yl)urea;
2-[4-methoxy-6-methyl-1,3,5-triazin-2-yl(methyl) carbamoylsulfamoyl]benzoic acid;
3-(4-methoxy-6-methyl-1,3,5-triazin-2-ylcarbamoylsulfamoyl)thiophen-2-carboxylic acid;
2-(4-methoxy-6-methyl-1,3,5-triazin-2-ylcarbamoylsulfamoyl)benzoic acid;
1-[2-(2-chloroethoxy)phenylsulfonyl]-3-(4-methoxy-6-methyl-1,3,5-triazin-2-yl)urea;
1-(4-methoxy-6-methyl-1,3,5-triazin-2-yl)-3-[2-(3,3,3-trifluoropropyl)-phenylsulfonyl]urea;
1-(4,6-dimethoxypyrimidin-2-yl)-3-(3-dimethylcarbamoyl-2-pyridylsulfonyl)urea;
2-[4,6-bis(difluoromethoxy)pyrimidin-2-yl-carbamoylsulfamoyl]benzoic acid;
N-[[(4,6-dimethoxy-2-pyrimidinyl)amino]carbonyl]-3-ethylsulfonyl-2-pyridinesulfonamide; and
1-(2-ethylsulfonylimidazo[1,2-a]pyridin-3-ylsulfonyl)-3-(4,6-dimethoxypyrimidin-2-yl)urea;
the weight ratio of (a) to (b) being from about 500:1 to about 1:50; and an agriculturally acceptable diluent or carrier therefor.

7. A composition comprising:
(a) a herbicidally effective amount, sufficient to elicit phytotoxicity in a crop plant, of a 4-benzoylisoxazole herbicide selected from the group consisting of:
5-cyclopropyl-4-(2-methylsulfonyl-4-trifluoromethyl) benzoylisoxazole;
ethyl 5-cyclopropyl-4-(2-methylsulfonyl-4-trifluoromethyl)benzoylisoxazole-3-carboxylate; and
ethyl 5-cyclopropyl-4-[3,4-dichloro-2-(methylthio) benzoylisoxazole-3-carboxylate; and (b) an effective phytotoxicity-reducing amount of at least one sulfonylurea herbicide selected from the group consisting of:
1-(2-chlorophenylsulfonyl)-3-(4-methoxy-6-methyl-1, 3,5-triazin-2-yl)urea;
2-[4-methoxy-6-methyl-1,3,5-triazin-2-yl(methyl) carbamoylsulfamoyl]benzoic acid;
3-(4-methoxy-6-methyl-1,3,5-triazin-2-ylcarbamoylsulfamoyl)thiophen-2-carboxylic acid;
2-(4-methoxy-6-methyl-1,3,5-triazin-2-ylcarbamoylsulfamoyl)benzoic acid;
1-[2-(2-chloroethoxy)phenylsulfonyl]-3-(4-methoxy-6-methyl-1,3,5-triazin-2-yl)urea;
1-(4-methoxy-6-methyl-1,3,5-triazin-2-yl)-3-[2-(3,3,3-trifluoropropyl)-phenylsulfonyl]urea;
1-(4,6-dimethoxypyrimidin-2-yl)-3-(3-dimethylcarbamoyl-2-pyridylsulfonyl)urea;
2-[4,6-bis(difluoromethoxy)pyrimidin-2-yl-carbamoylsulfamoyl]benzoic acid;
N-[[(4,6-dimethoxy-2-pyrimidinyl)amino]carbonyl]-3-ethylsulfonyl-2-pyridinesulfonamide; and
1-(2-ethylsulfonylimidazo[1,2-a]pyridin-3-ylsulfonyl)-3-(4,6-dimethoxypyrimidin-2-yl)urea;
the weight ratio of (a) to (b) being from about 500:1 to about 1:50; and an agriculturally acceptable diluent or carrier therefor.

8. A combination comprising a synergistic herbicidally effective amount of:
(a) a 4-benzoylisoxazole herbicide selected from the group consisting of:
5-cyclopropyl-4-(2-methylsulfonyl-4-trifluoromethyl) benzoylisoxazole;
ethyl 5-cyclopropyl-4-(2-methylsulfonyl-4-trifluoromethyl)benzoylisoxazole-3-carboxylate;
ethyl 5-cyclopropyl-4-[3,4-dichloro-2-(methylthio) benzoylisoxazole-3-carboxylate;
5-cyclopropyl-4-[4-bromo-2-(methylsulfonylmethyl) benzoylisoxazole;

5-cyclopropyl-4-(4-methylsulfonyl-2-trifluoromethyl) benzoylisoxazole; and 5-cyclopropyl-4-(4-chloro-2-methylsulfonyl) benzoylisoxazole; and (b) at least one sulfonylurea herbicide selected from the group consisting of:
1-(2-chlorophenylsulfonyl)-3-(4-methoxy-6-methyl-1,3,5-triazin-2-yl)urea;
2-[4-methoxy-6-methyl-1,3,5-triazin-2-yl(methyl) carbamoylsulfamoyl]-benzoic acid;
3-(4-methoxy-6-methyl-1,3,5-triazin-2-ylcarbamoylsulfamoyl)thiophen-2-carboxylic acid;
2-(4-methoxy-6-methyl-1,3,5-triazin-2-ylcarbamoyisulfamoyl)benzoic acid;
1-[2-(2-chloroethoxy)phenylsulfonyl]-3-(4-methoxy-6-methyl-1,3,5-triazin-2-yl)urea;
1-(4-methoxy-6-methyl-1,3,5-triazin-2-yl)-3-[2-(3,3,3-trifluoropropyl)-phenylsulfonyl]urea;
1-(4,6-dimethoxypyrimidin-2-yl)-3-(3-dimethyl-carbamoyl-2-pyridylsulfonyl)urea;
2-[4,6-bis(difluoromethoxy)pyrimidin-2-yl-carbamoylsulfamoyl]benzoic acid;
N-[[(4,6-dimethoxy-2-pyrimidinyl)amino]carbonyl]-3-ethylsulfonyl-2-pyridinesulfonamide; and
1-(2-ethylsulfonylimidazo[1,2-a]pyridin-3-ylsulfonyl)-3-(4,6-dimethoxypyrimidin-2-yl)urea;
the weight ratio of (a) to (b) being from about 500:1 to about 1:50.

9. A composition comprising:
(1) a synergistic herbicidally effective amount of:
(a) a 4-benzoylisoxazole herbicide selected from the group consisting of:
5-cyclopropyl-4-(2-methylsulfonyl-4-trifluoromethyl)benzoylisoxazole;
ethyl 5-cyclopropyl-4-(2-methylsulfonyl-4-trifluoromethyl)benzoylisoxazole-3-carboxylate;
ethyl 5-cyclopropyl-4-[3,4-dichloro-2-(methylthio) benzoylisoxazole-3-carboxylate;
5-cyclopropyl-4-[4-bromo-2-(methylsulfonyl-methyl)benzoylisoxazole;
5-cyclopropyl-4-(4-methylsulfonyl-2-trifluoromethyl)benzoylisoxazole; and
5-cyclopropyl-4-(4-chloro-2-methylsulfonyl) benzoylisoxazole; and
(b) at least one sulfonylurea herbicide selected from the group consisting of:
1-(2-chlorophenylsulfonyl)-3-(4-methoxy-6-methyl-1,3,5-triazin-2-yl)urea;
2-[4-methoxy-6-methyl-1,3,5-triazin-2-yl(methyl) carbamoylsulfamoyl]benzoic acid;
3-(4-methoxy-6-methyl-1,3,5-triazin-2-ylcarbamoylsulfamoyl)thiophen-2-carboxylic acid;
2-(4-methoxy-6-methyl-1,3,5-triazin-2-ylcarbamoylsulfamoyl)benzoic acid;
1-[2-(2-chloroethoxy)phenylsulfonyl]-3-(4-methoxy-6-methyl-1,3,5-triazin-2-yl)urea;
1-(4-methoxy-6-methyl-1,3,5-triazin-2-yl)-3-[2-(3,3,3-trifluoropropyl)-phenylsulfonyl]urea;
1-(4,6-dimethoxypyrimidin-2-yl)-3-(3-dimethylcarbamoyl-2-pyridylsulfonyl)urea;
2-[4,6-bis(difluoromethoxy)pyrimidin-2-yl-carbamoylsulfamoyl]benzoic acid;
N-[[(4,6-dimethoxy-2-pyrimidinyl)amino]carbonyl]-3-ethylsulfonyl-2-pyridinesulfonamide; and
1-(2-ethylsulfonylimidazo[1,2-a]pyridin-3-ylsulfonyl)-3-(4,6-dimethoxypyrimidin-2-yl)urea;

the weight ratio of (a) to (b) being from about 500:1 to about 1:50; and (2) an agriculturally acceptable diluent or carrier.

10. A composition consisting essentially of:
(a) a herbicidally effective amount, sufficient to elicit phytotoxicity in a crop plant, of a 4-benzoylisoxazole herbicide selected from the group consisting of:
5-cyclopropyl-4-(2-methylsulfonyl-4-trifluoromethyl) benzoylisoxazole;
ethyl 5-cyclopropyl-4-(2-methylsulfonyl-4-trifluoromethyl)benzoylisoxazole-3-carboxylate;
ethyl 5-cyclopropyl-4-[3,4-dichloro-2-(methylthio) benzoylisoxazole-3-carboxylate;
5-cyclopropyl-4-[4-bromo-2-(methylsulfonylmethyl) benzoylisoxazole;
5-cyclopropyl-4-(4-methylsulfonyl-2-trifluoromethyl) benzoylisoxazole; and
5-cyclopropyl-4-(4-chloro-2-methylsulfonyl) benzoylisoxazole; and
(b) an effective phytoxicity-reducing amount of at least one sulfonylurea herbicide selected from the group consisting of:
1-(2-chlorophenylsulfonyl)-3-(4-methoxy-6-methyl-1,3,5-triazin-2-yl)urea;
2-[4-methoxy-6-methyl-1,3,5-triazin-2-yl(methyl) carbamoylsulfamoyl]benzoic acid;
3-(4-methoxy-6-methyl-1,3,5-triazin-2-ylcarbamoylsulfamoyl)thiophen-2-carboxylic acid;
2-(4-methoxy-6-methyl-1,3,5-triazin-2-ylcarbamoylsulfamoyl)benzoic acid;
1-[2-(2-chloroethoxy)phenylsulfonyl]-3-(4-methoxy-6-methyl-1,3,5-triazin-2-yl)urea;
1-(4-methoxy-6-methyl-1,3,5-triazin-2-yl)-3-[2-(3,3,3-trifluoropropyl)-phenylsulfonyl]urea;
1-(4,6-dimethoxypyrimidin-2-yl)-3-(3-dimethylcarbamoyl-2-pyridylsulfonyl)urea;
2-[4,6-bis(difluoromethoxy)pyrimidin-2-yl-carbamoylsulfamoyl]benzoic acid;
N-[[(4,6-dimethoxy-2-pyrimidinyl)amino]carbonyl]-3-ethylsulfonyl-2-pyridinesulfonamide; and
1-(2-ethylsulfonylimidazo[1,2-a]pyridin-3-ylsulfonyl)-3-(4,6-dimethoxypyrimidin-2-yl)urea;

the weight ratio of (a) to (b) being from about 500:1 to about 1:50; and an agriculturally acceptable diluent or carrier therefor.

11. A composition consisting essentially of:
(a) a herbicidally effective amount, sufficient to elicit phytotoxicity in a crop plant, of a 4-benzoylisoxazole herbicide selected from the group consisting of:
5-cyclopropyl-4-(2-methylsulfonyl-4-trifluoromethyl) benzoylisoxazle;
ethyl 5-cyclopropyl-4-(2-methylsulfonyl-4-trifluoromethyl)benzoylisoxazole-3-carboxylate; and
ethyl 5-cyclopropyl-4-[3,4-dichloro-2-(methylthio) benzoylisoxazole-3-carboxylate; and
(b) an effective phytoxicity-reducing amount of at least one sulfonylurea herbicide selected from the group consisting of:
1-(2-chlorophenylsulfonyl)-3-(4-methoxy-6-methyl-1,3,5-triazin-2-yl)urea;
2-[4-methoxy-6-methyl-1,3,5-triazin-2-yl(methyl) carbamoylsulfamoyl]benzoic acid;
3-(4-methoxy-6-methyl-1,3,5-triazin-2-ylcarbamoylsulfamoyl)thiophen-2-carboxylic acid;
2-(4-methoxy-6-methyl-1,3,5-triazin-2-ylcarbamoylsulfamoyl)benzoic acid;

1-[2-(2-chloroethoxy)phenylsulfonyl]-3-(4-methoxy-6-methyl-1,3,5-triazin-2-yl)urea;
1-(4-methoxy-6-methyl-1,3,5-triazin-2-yl)-3-[2-(3,3,3-trifluoropropyl)-phenylsulfonyl]urea;
1-(4,6-dimethoxypyrimidin-2-yl)-3-(3-dimethylcarbamoyl-2-pyridylsulfonyl)urea;
2-[4,6-bis(difluoromethoxy)pyrimidin-2-ylcarbamoylsulfamoyl]benzoic acid;
N-[[(4,6-dimethoxy-2-pyrimidinyl)amino]carbonyl]-3-ethylsulfonyl-2-pyridinesulfonamide; and
1-(2-ethylsulfonylimidazo[1,2-a]pyridin-3-ylsulfonyl)-3-(4,6-dimethoxypyrimidin-2-yl)urea;
the weight ratio of (a) to (b) being from about 500:1 to about 1:50; and an agriculturally acceptable diluent or carrier therefor.

12. A combination consisting essentially of a synergistic herbicidally effective amount of:
(a) a 4-benzoylisoxazole herbicide selected from the group consisting of:
5-cyclopropyl-4-(2-methylsulfonyl-4-trifluoromethyl)benzoylisoxazole;
ethyl 5-cyclopropyl-4-(2-methylsulfonyl-4-trifluoromethyl)benzoylisoxazole-3-carboxylate;
ethyl 5-cyclopropyl-4-[3,4-dichloro-2-(methylthio)benzoylisoxazole-3-carboxylate;
5-cyclopropyl-4-[4-bromo-2-(methylsulfonylmethyl)benzoylisoxazole;
5-cyclopropyl-4-(4-methylsulfonyl-2-trifluoromethyl)benzoylisoxazole; and
5-cyclopropyl-4-(4-chloro-2-methylsulfonyl)benzoylisoxazole; and
(b) at least one sulfonylurea herbicide selected from the group consisting of:
1-(2-chlorophenylsulfonyl)-3-(4-methoxy-6-methyl-1,3,5-triazin-2-yl)urea;
2-[4-methoxy-6-methyl-1,3,5-triazin-2-yl(methyl)carbamoylsulfamoyl]benzoic acid;
3-(4-methoxy-6-methyl-1,3,5-triazin-2-ylcarbamoylsulfamoyl)thiophen-2-carboxylic acid;
2-(4-methoxy-6-methyl-1,3,5-triazin-2-ylcarbamoylsulfamoyl)benzoic acid;
1-[2-(2-chloroethoxy)phenylsulfonyl]-3-(4-methoxy-6-methyl-1,3,5-triazin-2-yl)urea;
1-(4-methoxy-6-methyl-1,3,5-triazin-2-yl)-3-[2-(3,3,3-trifluoropropyl)-phenylsulfonyl]urea;
1-(4,6-dimethoxypyrimidin-2-yl)-3-(3-dimethylcarbamoyl-2-pyridylsulfonyl)urea;
2-[4,6-bis(difluoromethoxy)pyrimidin-2-ylcarbamoylsulfamoyl]benzoic acid;
N-[[(4,6-dimethoxy-2-pyrimidinyl)amino]carbonyl]-3-ethylsulfonyl-2-pyridinesulfonamide; and
1-(2-ethylsulfonylimidazo[1,2-a]pyridin-3-ylsulfonyl)-3-(4,6-dimethoxypyrimidin-2-yl)urea;
the weight ratio of (a) to (b) being from about 500:1 to about 1:50.

13. A composition consisting essentially of:
(1) a synergistic herbicidally effective amount of:
(a) a 4-benzoylisoxazole herbicide selected from the group consisting of:
5-cyclopropyl-4-(2-methylsulfonyl-4-trifluoromethyl)benzoylisoxazole;
ethyl 5-cyclopropyl-4-(2-methylsulfonyl-4-trifluoromethyl)benzoylisoxazole-3-carboxylate;
ethyl 5-cyclopropyl-4-[3,4-dichloro-2-(methylthio)benzoylisoxazole-3-carboxylate;
5-cyclopropyl-4-[4-bromo-2-(methylsulfonylmethyl)benzoylisoxazole;
5-cyclopropyl-4-(4-methylsulfonyl-2-trifluoromethyl)benzoylisoxazole; and
5-cyclopropyl-4-(4-chloro-2-methylsulfonyl)benzoylisoxazole; and
(b) at least one sulfonylurea herbicide selected from the group consisting of:
1-(2-chlorophenylsulfonyl)-3-(4-methoxy-6-methyl-1,3,5-triazin-2-yl)urea;
2-[4-methoxy-6-methyl-1,3,5-triazin-2-yl(methyl)carbamoylsulfamoyl]benzoic acid;
3-(4-methoxy-6-methyl-1,3,5-triazin-2-ylcarbamoylsulfamoyl)thiophen-2-carboxylic acid;
2-(4-methoxy-6-methyl-1,3,5-triazin-2-ylcarbamoylsulfamoyl)benzoic acid;
1-[2-(2-chloroethoxy)phenylsulfonyl]-3-(4-methoxy-6-methyl-1,3,5-triazin-2-yl)urea;
1-(4-methoxy-6-methyl-1,3,5-triazin-2-yl)-3-[2-(3,3,3-trifluoropropyl)-phenylsulfonyl]urea;
1-(4,6-dimethoxypyrimidin-2-yl)-3-(3-dimethylcarbamoyl-2-pyridylsulfonyl)urea;
2-[4,6-bis(difluoromethoxy)pyrimidin-2-ylcarbamoylsulfamoyl]benzoic acid;
N-[[(4,6-dimethoxy-2-pyrimidinyl)amino]carbonyl]-3-ethylsulfonyl-2-pyridinesulfonamide; and
1-(2-ethylsulfonylimidazo[1,2-a]pyridin-3-ylsulfonyl)-3-(4,6-dimethoxypyrimidin-2-yl)urea;
the weight ratio of (a) to (b) being from about 500:1 to about 1:50; and
(2) an agriculturally acceptable diluent or carrier.

14. A method for reducing phytotoxicity in a crop plant in need of same, said phytotoxicity in said crop plant resulting from treatment with a 4-benzoylisoxazole herbicide, said method comprising applying to said crop plant, to its locus or to its seed, a combination consisting essentially of:
(a) a herbicidally effective amount, sufficient to elicit phytotoxicity in said crop plant, of a 4-benzoylisoxazole herbicide selected from the group consisting of:
5-cyclopropyl-4-(2-methylsulfonyl-4-trifluoromethyl)benzoylisoxazole;
ethyl 5-cyclopropyl-4-(2-methylsulfonyl-4-trifluoromethyl)benzoylisoxazole-3-carboxylate;
ethyl 5-cyclopropyl-4-[3,4-dichloro-2-(methylthio)benzoylisoxazole-3-carboxylate;
5-cyclopropyl-4-[4-bromo-2-(methylsulfonylmethyl)benzoylisoxazole;
5-cyclopropyl-4-(4-methylsulfonyl-2-trifluoromethyl)benzoylisoxazole; and
5-cyclopropyl-4-(4-chloro-2-methylsulfonyl)benzoylisoxazole; and
(b) an effective phytoxicity-reducing amount of at least one sulfonylurea herbicide selected from the group consisting of:
1-(2-chlorophenylsulfonyl)-3-(4-methoxy-6-methyl-1,3,5-triazin-2-yl)urea;
2-[4-methoxy-6-methyl-1,3,5-triazin-2-yl(methyl)carbamoylsulfamoyl]benzoic acid;
3-(4-methoxy-6-methyl-1,3,5-triazin-2-ylcarbamoylsulfamoyl)thiophen-2-carboxylic acid;
2-(4-methoxy-6-methyl-1,3,5-triazin-2-ylcarbamoylsulfamoyl)benzoic acid;
1-[2-(2-chloroethoxy)phenylsulfonyl]-3-(4-methoxy-6-methyl-1,3,5-triazin-2-yl)urea;
1-(4-methoxy-6-methyl-1,3,5-triazin-2-yl)-3-[2-(3,3,3-trifluoropropyl)-phenylsulfonyl]urea;

1-(4,6-dimethoxypyrimidin-2-yl)-3-(3-dimethyl-carbamoyl-2-pyridylsulfonyl)urea;

2-[4,6-bis(difluoromethoxy)pyrimidin-2-yl-carbamoylsulfamoyl]benzoic acid;

N-[[(4,6-dimethoxy-2-pyrimidinyl)amino]carbonyl]-3-ethylsulfonyl-2-pyridinesulfonamide; and 1-(2-ethylsulfonylimidazo[1,2-a]pyridin-3-ylsulfonyl)-3-(4,6-dimethoxypyrimidin-2-yl)urea;

the weight ratio of (a) to (b) being from about 500:1 to about 1:50.

15. A method according to claim 5, wherein the 4-benzoylisoxazole herbicide is 5-cyclopropyl-4-(2-methylsulfonyl-4-trifluoromethyl)-benzoylisoxazole.

16. A method according to claim 5, wherein the 4-benzoylisoxazole herbicide is ethyl 5-cyclopropyl 4-(2-methylsulfonyl-4-trifluoromethylbenzoyl)-isoxazole-3-carboxylate.

17. A method according to claim 5, wherein the 4-benzoylisoxazole herbicide is ethyl 5-cyclopropyl-4-[3,4-dichloro-2-(methylthio)benzoyl]-isoxazole-3-carboxylate.

18. A method according to claim 1, wherein the crop plant is corn, rice, wheat, soya, sorghum or cotton.

19. A method according to claim 1, wherein the crop plant is wheat.

20. A method according to claim 1, wherein the dose rate of (a) is from about 5 to about 500 g/ha.

21. A method according to claim 1, wherein the dose rate of the sulfonylurea herbicide is from about 1 to about 250 g/ha.

22. A composition according to claim 6, wherein the phytotoxicity-reducing amount of the sulfonylurea herbicide is an amount which is less than that at which the sulfonylurea herbicide is herbicidally effective.

23. A composition according to claim 7, wherein the 4-benzoylisoxazole herbicide is 5-cyclopropyl-4-(2-methylsulfonyl-4-trifluoromethyl)benzoylisoxazole.

24. A composition according to claim 7, wherein the 4-benzoylisoxazole herbicide is ethyl 5-cyclopropyl-4-(2-methylsulfonyl-4-trifluoromethylbenzoyl)isoxazole-3-carboxylate.

25. A composition according to claim 7, wherein the 4-benzoylisoxazole herbicide is ethyl 5-cyclopropyl-4-[3,4-dichloro-2-(methylthio)benzoyl]isoxazole-3-carboxylate.

26. A composition according to claim 9, wherein the 4-benzoylisoxazole herbicide is 5-cyclopropyl-4-(2-methylsulfonyl-4-trifluoromethyl)benzoylisoxazole.

27. A composition according to claim 9, wherein the 4-benzoylisoxazole herbicide is ethyl 5-cyclopropyl-4-(2-methylsulfonyl-4-trifluoromethylbenzoyl)isoxazole-3-carboxylate.

28. A composition according to claim 9, wherein the 4-benzoylisoxazole herbicide is ethyl 5-cyclopropyl-4-[3,4-dichloro-2-(methylthio)benzoyl]isoxazole-3-carboxylate.

29. A method for reducing phytotoxicity in a crop plant in need of same, said phytotoxicity in said crop plant resulting from treatment with a 4-benzoylisoxazole herbicide, said method comprising applying to said crop plant, or to its locus, a combination consisting essentially of:

(a) a herbicidally effective amount, sufficient to elicit phytotoxicity in said crop plant, of a 4-benzoylisoxazole herbicide selected from the group consisting of:
5-cyclopropyl-4-(2-methylsulfonyl-4-trifluoromethyl) benzoylisoxazole;
ethyl 5-cyclopropyl-4-(2-methylsulfonyl-4-trifluoromethyl)benzoylisoxazole-3-carboxylate; and
ethyl 5-cyclopropyl-4-[3,4-dichloro-2-(methylthio) benzoylisoxazole-3-carboxylate; and (b) an effective phytotoxicity-reducing amount of at least one sulfonylurea herbicide selected from the group consisting of:
1-(2-chlorophenylsulfonyl)-3-(4-methoxy-6-methyl-1,3,5-triazin-2-yl)urea;
2-[4-methoxy-6-methyl-1,3,5-triazin-2-yl(methyl) carbamoylsulfamoyl]benzoic acid;
3-(4-methoxy-6-methyl-1,3,5-triazin-2-ylcarbamoylsulfamoyl)thiophen-2-carboxylic acid;
2-(4-methoxy-6-methyl-1,3,5-triazin-2-ylcarbamoylsulfamoyl)benzoic acid;
1-[2-(2-chloroethoxy)phenylsulfonyl]-3-(4-methoxy-6-methyl-1,3,5-triazin-2-yl)urea;
1-(4-methoxy-6-methyl-1,3,5-triazin-2-yl)-3-[2-(3,3,3-trifluoropropyl)-phenylsulfonyl]urea;
1-(4,6-dimethoxypyrimidin-2-yl)-3-(3-dimethyl-carbamoyl-2-pyridylsulfonyl)urea;
2-[4,6-bis(difluoromethoxy)pyrimidin-2-yl-carbamoylsulfamoyl]benzoic acid;
N-[[(4,6-dimethoxy-2-pyrimidinyl)amino]carbonyl]-3-ethylsulfonyl-2-pyridinesulfonamide; and
1-(2-ethylsulfonylimidazo[1,2-a]pyridin-3-ylsulfonyl)-3-(4,6-dimethoxypyrimidin-2-yl)urea;

the weight ratio of (a) to (b) being from about 500:1 to about 1:50.

30. A method for reducing phytotoxicity in a crop plant in need of same, said phytotoxicity in said crop plant resulting from treatment with a 4-benzoylisoxazole herbicide, said method comprising applying to said crop plant, to its locus or to its seed, a composition consisting essentially of:

(a) a herbicidally effective amount, sufficient to elicit phytotoxicity in said crop plant, of a 4-benzoylisoxazole herbicide selected from the group consisting of:
5-cyclopropyl-4-(2-methylsulfonyl-4-trifluoromethyl) benzoylisoxazole;
ethyl 5-cyclopropyl-4-(2-methylsulfonyl-4-trifluoromethyl)benzoylisoxazole-3-carboxylate;
ethyl 5-cyclopropyl-4-[3,4-dichloro-2-(methylthio) benzoylisoxazole-3-carboxylate;
5-cyclopropyl-4-[4-bromo-2-(methylsulfonylmethyl) benzoylisoxazole;
5-cyclopropyl-4-(4-methylsulfonyl-2-trifluoromethyl) benzoylisoxazole; and
5-cyclopropyl-4-(4-chloro-2-methylsulfonyl) benzoylisoxazole; and (b) an effective phytotoxicity-reducing amount of at least one sulfonylurea herbicide selected from the group consisting of:
1-(2-chlorophenylsulfonyl)-3-(4-methoxy-6-methyl-1,3,5-triazin-2-yl)urea;
2-[4-methoxy-6-methyl-1,3,5-triazin-2-yl(methyl) carbamoylsulfamoyl]benzoic acid;
3-(4-methoxy-6-methyl-1,3,5-triazin-2-ylcarbamoylsulfamoyl)thiophen-2-carboxylic acid;
2-(4-methoxy-6-methyl-1,3,5-triazin-2-ylcarbamoylsulfamoyl)benzoic acid;
1-[2-(2-chloroethoxy)phenylsulfonyl]-3-(4-methoxy-6-methyl-1,3,5-triazin-2-yl)urea;
1-(4-methoxy-6-methyl-1,3,5-triazin-2-yl)-3-[2-(3,3,3-trifluoropropyl)-phenylsulfonyl]urea;
1-(4,6-dimethoxypyrimidin-2-yl)-3-(3-dimethyl-carbamoyl-2-pyridylsulfonyl)urea;
2-[4,6-bis(difluoromethoxy)pyrimidin-2-yl-carbamoylsulfamoyl]benzoic acid;
N-[[(4,6-dimethoxy-2-pyrimidinyl)amino]carbonyl]-3-ethylsulfonyl-2-pyridinesulfonamide; and 1-(2-ethylsulfonylimidazo[1,2-a]pyridin-3-ylsulfonyl)-
3-(4,6-dimethoxypyrimidin-2-yl)urea;
the weight ratio of (a) to (b) being from about 500:1 to
about 1:50; and an agriculturally acceptable diluent or
carrier therefor.

31. A method for reducing phytotoxicity in a crop plant in need of same, said phytotoxicity in said crop plant resulting from treatment with a 4-benzoylisoxazole herbicide, said method comprising applying to said crop plant, or to its locus, a composition consisting essentially of:
(a) a herbicidally effective amount, sufficient to elicit phytotoxicity in said crop plant, of a 4-benzoylisoxazole herbicide selected from the group consisting of:
5-cyclopropyl-4-(2-methylsulfonyl-4-trifluoromethyl) benzoylisoxazole;
ethyl 5-cyclopropyl-4-(2-methylsulfonyl-4-trifluoromethyl)benzoylisoxazole-3-carboxylate; and
ethyl 5-cyclopropyl4-[3,4-dichloro-2-(methylthio) benzoylisoxazole-3-carboxylate; and
(b) an effective phytotoxicity-reducing amount of at least one sulfonylurea herbicide selected from the group consisting of:
1-(2-chlorophenyisulfonyl)-3-(4-methoxy-6-methyl-1, 3,5-triazin-2-yl)urea;
2-[4-methoxy-6-methyl-1,3,5-triazin-2-yl(methyl) carbamoylsulfamoyl]benzoic acid;
3-(4-methoxy-6-methyl-1,3,5-triazin-2-ylcarbamoylsulfamoyl)thiophen-2-carboxylic acid;
2-(4-methoxy-6-methyl-1,3,5-triazin-2-ylcarbamoylsulfamoyl)benzoic acid;
1-[2-(2-chloroethoxy)phenylsulfonyl]-3-(4-methoxy-6-methyl-1,3,5-triazin-2-yl)urea;
1-(4-methoxy-6-methyl-1,3,5-triazin-2-yl)-3-[2-(3,3,3-trifluoropropyl)-phenylsulfonyl]urea;
1-(4,6-dimethoxypyrimidin-2-yl)-3-(3-dimethyl-carbamoyl-2-pyridylsulfonyl)urea;
2-[4,6-bis(difluoromethoxy)pyrimidin-2-yl-carbamoylsulfamoyl]benzoic acid;
N-[[(4,6-dimethoxy-2-pyrimidinyl)amino]carbonyl]-3-ethylsulfonyl-2-pyridinesulfonamide; and
1-(2-ethylsulfonylimidazo[1,2-a]pyridin-3-ylsulfonyl)-3-(4,6-dimethoxypyrimidin-2-yl)urea;
the weight ratio of (a) to (b) being from about 500:1 to about 1:50; and an agriculturally acceptable diluent or carrier therefor.

32. A method according to claim 29, wherein the 4-benzoylisoxazole herbicide is 5-cyclopropyl-4-(2-methylsulfonyl-4-trifluoromethyl)benzoylisoxazole.

33. A method according to claim 29, wherein the 4-benzoylisoxazole herbicide is ethyl 5-cyclopropyl 4-(2-methylsulfonyl-4-trifluoromethylbenzoyl)isoxazole-3-carboxylate.

34. A method according to claim 29, wherein the 4-benzoylisoxazole herbicide is ethyl 5-cyclopropyl-4-[3,4-dichloro-2-(methylthio)benzoyl]isoxazole-3-carboxylate.

35. A method according to claim 5, wherein the crop plant is corn, rice, wheat, soya, sorghum or cotton.

36. A method according to claim 5, wherein the crop plant is wheat.

37. A method according to claim 5, wherein the dose rate of (a) is from about 5 to about 500 g/ha.

38. A method according to claim 14, wherein the crop plant is corn, rice, wheat, soya, sorghum or cotton.

39. A method according to claim 14, wherein the crop plant is wheat.

40. A method according to claim 14, wherein the dose rate of (a) is from about 5 to about 500 g/ha.

41. A method according to claim 29, wherein the crop plant is corn, rice, wheat, soya, sorghum or cotton.

42. A method according to claim 29, wherein the crop plant is wheat.

43. A method according to claim 29, wherein the dose rate of (a) is from about 5 to about 500 g/ha.

44. A method according to claim 5, wherein the dose rate of the sulfonylurea herbicide is from about 1 to about 250 g/ha.

45. A method according to claim 14, wherein the dose rate of the sulfonylurea herbicide is from about 1 to about 250 g/ha.

46. A method according to claim 29, wherein the dose rate of the sulfonylurea herbicide is from about 1 to about 250 g/ha.

47. A method according to claim 5, wherein the 4-benzoylisoxazole herbicide is 5-cyclopropyl-4-(2-methylsulfonyl-4-trifluoromethyl)benzoylisoxazole and the sulfonylurea herbicide is thifensulfuron methyl and tribenuron methyl.

48. A method according to claim 29, wherein the 4-benzoylisoxazole herbicide is 5-cyclopropyl-4-(2-methylsulfonyl-4-trifluoromethyl)benzoylisoxazole and the sulfonylurea herbicide is thifensulfuron methyl and tribenuron methyl.

49. A method according to claim 5, wherein the 4-benzoylisoxazole herbicide is ethyl 5-cyclopropyl-4-(2-methylsulfonyl-4-trifluoromethyl)benzoylisoxazole-3-carboxylate and the sulfonylurea herbicide is thifensulfuron methyl and tribenuron methyl.

50. A method according to claim 29, wherein the 4-benzoylisoxazole herbicide is ethyl 5-cyclopropyl-4-(2-methylsulfonyl-4-trifluoromethyl)benzoylisoxazole-3-carboxylate and the sulfonylurea herbicide is thifensulfuron methyl and tribenuron methyl.

51. A method according to claim 5, wherein the 4-benzoylisoxazole herbicide is ethyl 5-cyclopropyl-4-[3,4-dichloro-2-(methylthio)benzoyl]isoxazole-3-carboxylate and the sulfonylurea herbicide is prosulfuron.

52. A method according to claim 14, wherein the 4-benzoylisoxazole herbicide is ethyl 5-cyclopropyl-4-[3,4-dichloro-2-(methylthio)benzoyl]isoxazole-3-carboxylate and the sulfonylurea herbicide is prosulfuron.

53. A composition according to claim 10, wherein the phytotoxicity-reducing amount of the sulfonylurea herbicide is an amount which is less than that at which the sulfonylurea herbicide is herbicidally active.

54. A composition according to claim 11, wherein the 4-benzoylisoxazole herbicide is 5-cyclopropyl-4-(2-methylsulfonyl-4-trifluromethyl)benzoylisoxazole.

55. A composition according to claim 11, wherein the 4-benzoylisoxazole herbicide is ethyl 5-cyclopropyl-4-(2-methylsulfonyl-4-trifluoromethylbenzoyl)isoxazole-3-carboxylate.

56. A composition according to claim 11, wherein the 4-benzoylisoxazole herbicide is ethyl 5-cyclopropyl-4-[3,4-dichloro-2-(methylthio)benzoyl]isoxazole-3-carboxylate.

57. A composition according to claim 13, wherein the 4-benzoylisoxazole herbicide is 5-cyclopropyl-4-(2-methylsulfonyl-4-trifluoromethyl)benzoylisoxazole.

58. A composition according to claim 13, wherein the 4-benzoylisoxazole herbicide is ethyl 5-cyclopropyl-4-(2-methylsulfonyl-4-trifluoromethylbenzoyl)isoxazole-3-carboxylate.

59. A composition according to claim 13, wherein the 4-benzoylisoxazole herbicide is ethyl 5-cyclopropyl-4-[3,4-dichloro-2-(methylthio)benzoyl]isoxazole-3-carboxylate.

* * * * *